(12) United States Patent
Roth et al.

(10) Patent No.: US 6,762,031 B2
(45) Date of Patent: Jul. 13, 2004

(54) TARGETING VIRAL VECTORS TO SPECIFIC CELLS

(75) Inventors: Monica Judith Roth, New York, NY (US); Keith Bupp, Somerset, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 64 days.

(21) Appl. No.: 09/881,572

(22) Filed: Jun. 14, 2001

(65) Prior Publication Data

US 2002/0164583 A1 Nov. 7, 2002

Related U.S. Application Data

(60) Provisional application No. 60/212,239, filed on Jun. 16, 2000.

(51) Int. Cl.[7] ............................... G01N 33/53
(52) U.S. Cl. .............................. 435/7.2; 435/7.1; 435/6; 435/5; 435/4; 435/DIG. 4; 435/DIG. 3; 435/DIG. 2; 536/23.72; 536/23.1; 530/403
(58) Field of Search ............................... 435/7.2, 7.1, 6, 435/5, 4, DIG. 4.2; 536/23.72, 23.1; 530/403

(56) References Cited

U.S. PATENT DOCUMENTS

| | | | |
|---|---|---|---|
| 5,714,374 A | 2/1998 | Arnold et al. | |
| 5,723,287 A | 3/1998 | Russell et al. | |
| 5,766,899 A | 6/1998 | Kuo et al. | |
| 5,869,331 A | 2/1999 | Dornburg | |
| 5,871,727 A | 2/1999 | Curiel | |
| 5,885,808 A | 3/1999 | Spooner et al. | |
| 5,998,192 A | 12/1999 | Russell et al. | |
| 6,031,071 A | 2/2000 | Mandeville et al. | |
| 6,060,316 A | 5/2000 | Young et al. | |
| 6,096,548 A | 8/2000 | Stemmer | |
| 6,146,885 A | 11/2000 | Dornburg | |
| 6,168,916 B1 | 1/2001 | Kingsman | |
| 6,297,004 B1 | 10/2001 | Russell et al. | |
| 6,312,699 B1 | 11/2001 | Curiel et al. | |
| 6,329,190 B1 | 12/2001 | Wickham et al. | |
| 6,410,313 B1 | 6/2002 | Kasahara et al. | |
| 6,451,527 B1 * | 9/2002 | Larocca et al. | 435/6 |
| 6,455,247 B1 * | 9/2002 | Nolan et al. | 435/6 |

OTHER PUBLICATIONS

Battini et al, PNAS, 96, 1385–90 (Feb. 1999).*
Keith Bupp and Monica J. Roth, Altering Retroviral Tropism Using a Random–Display Envelope Library, Molecular Therapy, Mar. 2002, 5:329–335.
Lavilette et al., Retargeting Gene Delivery Using Surface–engineered Retroviral Vector Particles, Current Opinion in Biotechnology, 2001, 12:461–466.
Soong et al., Molecular Breeding of Viruses, Nature Genetics, Aug. 2000, 25:436–439.
Wu et al., Identification of Regions in the Moloney Murine Leukemia Virus SU Protein That Tolerate the Insertion of an Integrin–Binding Peptide, Virology, 2000, 269:7–17.
Keith Bupp and Monica J. Roth, Strategies and Mechanisms for Retrovirus Retargeting, Viral Vectors: Basic Science and Gene Therapy, 2000, 379–399.
Buchholz et al., In Vivo Selection of Protease Cleavage Sites from Retrovirus Display Libraries, Nature Biotechnology, Oct. 1998, vol. 16, 951–954.
Powell et al., Breeding of Retroviruses by DNA Shuffling for Improved Stability and Processing Yields, Nature Biotechnology, Dec. 2000, 18:1279–1282.

* cited by examiner

Primary Examiner—T. D. Wessendorf
(74) Attorney, Agent, or Firm—Klauber & Jackson

(57) ABSTRACT

Methods for creating viral display libraries for purposes of isolating variants with modified target cell specificity and related methods; also retroviral display libraries.

3 Claims, 13 Drawing Sheets

```
              46            50              60            70    74
VRA  4070A    D L V G E E W D P S D Q E P Y V G C K Y P A G R Q R T
     Mo-MCF           I D D   E T – – – – –   L       R T G K   A 129             140             150         157
VRB  4070A    P W D T G C S K V A C G P C Y D L S K V S N S F Q G A T R
```

Figure 2

```
FeLV A    ⁴⁸V G D T W E P I V L N P T N V K H G A R Y S S S K Y G C K⁷⁶
FeLV C    ⁴⁸V G D T W E P M A P D P - - R S W A R Y S S S T H G C K⁷³
4070A     ⁴⁸V G E E W D P S D Q E P - - - - Y V G Y - - - - G C K⁶⁶
```

```
FeLV-A   W E P I V L D P T N V K H G A R Y P S S K Y G C
C subst  W E P M A P D P - - - R S W A R Y S S S I H G C
Random   W E P X X X X X - - - R X X X X X S S S K Y G C
```

FIGURE 6

```
5'  GTGGGAGACACCTGGGAACCT (NNN)₅ AGA (NNN)₅ TCCTCCTCAAAATATGGA 3'
3'         CTCTGTGGACCCTTGGA 5'          3' AGGAGGAGTTTTATACCTACAT 5'
```

FIGURE 8

```
FeLV-A   W E P I V L D P T N V K H G - A R Y P S S K Y G C
RANTES   W E P X X X S P Y S S D T T P A X X X S S K Y G C
```

TARGETING VIRAL VECTORS TO SPECIFIC CELLS

CROSS REFERENCE TO RELATED APPLICATIONS

This application claims priority of U.S. Ser. No. 60/212,239, filed Jun. 16, 2000.

The research leading to the present invention was supported, at least in part, by grant 1ROI CA49932 from the National Institutes of Health. Accordingly, the Government may have certain rights in the invention.

BACKGROUND

This invention relates to the field of viral constructs, especially their use in gene delivery.

Targeting of a retroviral gene delivery vehicle specifically to the tissue where expression of a transgene is required is a critical aspect of gene therapy. In order to retarget a retrovirus to a tissue of interest, three basic strategies have been widely used to alter retroviral interactions with cellular receptors:

1) Complete substitution of the envelope glycoprotein (Env) by another protein.

2) Incorporation of an antibody fragment into Env.

3) Incorporation of a cell-binding ligand into Env.

Fusing a cell-binding ligand or single-chain antibody fragment to Env only rarely leads to reasonably efficient retargeted gene transfer. The lack of success using these approaches may be due to structural perturbations of the Env molecule as a result of fusion to the novel targeting domain. The present invention reflects an alternative approach to avoid this problem.

SUMMARY OF THE INVENTION

In a general aspect, the invention is a retroviral display library, said library comprising a plurality (preferably more than $1\times10^5$, more preferably more than $1\times10^6$) of retroviruses wherein each retrovirus differs in relation to other retroviruses in the plurality as to the amino acid sequence of an Env protein, each member of the plurality comprising nucleic acid that codes for both said Env protein and a cell-selection marker.

In a general aspect, the invention is a retroviral Env library, said library comprising a plurality (preferably more than $1\times10^5$, more preferably more than $1\times10^6$) of Env proteins wherein the amino acid sequence of each Env protein differs in relation to the amino acid sequence of the other Env proteins in the plurality.

In another related aspect, the invention is a retroviral nucleic acid library said library comprising a plurality (preferably more than $1\times10^5$, more preferably more than $1\times10^6$) of retroviral nucleic acid molecules, each of said molecules coding for a retroviral Env protein and a cell-selection marker, and wherein each of said nucleic acid molecule differs in relation to other nucleic acid molecules in the plurality as to the Env protein amino acid sequence that it codes for.

In another related aspect, the invention is a cell population expressing either a retroviral display library or a retroviral Env library or a retroviral Env library of the present invention. Preferably, the population is one that has achieved (or is capable of) such expression through at least 10 (more preferably at least 200) cell population doublings.

In several related aspects, the invention is method. Each of these methods is applicable to any virus. Nevertheless, in one preferred set of embodiments, the virus that forms the basis for the library is one that infects mammalian cells (e.g., human cells). In another preferred set of embodiments, the virus is one of a kind that has been used in gene delivery experiments by others, and includes retroviruses, adenoviruses, herpes viruses, and adeno-associated viruses and alphaviruses. Retroviruses are of particular interest and, in the case of retroviruses, the exterior protein of the virus is preferably an Env protein.

In one aspect, applicable to all viruses, the invention is a method of creating a viral display library said method comprising the steps of:

(1) randomly integrating nucleotides (by adding or, more preferably, substituting nucleotides) into viral nucleic acid molecules, the site of said integration in each nucleic acid molecule being within the coding region for an exterior protein of said virus, so as to create a library of viral nucleic acid molecules; and (2) infecting a population of cells with the nucleic molecules created in step (1) so as to create a library comprising a plurality (preferably more than $1\times10^5$, more preferably more than $1\times10^6$) of viruses wherein for each member of the plurality, the amino acid sequence of the exterior protein coded for by the nucleic acid molecule differs from the amino acid sequence of exterior protein coded for by other members of the plurality, and wherein prior to step (2) (preferably prior to step (1)) each of said nucleic acid molecules further comprises a coding sequence for a cell-selection marker.

In another aspect applicable to all viruses, the invention is a method of isolating a virus that can transfer its nucleic acid to a host cell, said method comprising the steps of:

(1) administering to a population of host cells, a random display library of viruses comprising a plurality (preferably more than $1\times10^5$, more preferably more than $1\times10^6$) of viruses, wherein each virus differs in relation to other viruses of the plurality as to the amino acid sequence of the exterior protein; and (2) isolating a virus that infected one of said host cells. In one embodiment, each member of the plurality codes, on the same nucleic acid molecule, for both an exterior protein of the virus and a cell-selection marker and step (2) can be achieved by cell selection for virus-infected cells. Alternatively, virus that infected the cells can be identified, after a suitable delay post-infection, in the cell supernatant. For retroviruses, the identification can be made, generally 1 to 2 weeks post infection, by assaying for retroviral reverse transcriptase (Goff, S. P., Traktman, P., and D. Baltimore (1981) J. Virol. 38:239–248).

In another aspect applicable to all viruses, the invention is a method of transmitting non-viral nucleic acid (preferably a gene expressible in said cell., it being understood that the gene can be transmitted as RNA, incorporated into the cell genome as DNA, and be expressed) to a cell, said method comprising the steps of:

(1) administering to a population of host cells, a random display library of viruses, comprising a plurality (preferably more than $1\times10^5$, more preferably more than $1\times10^6$) of viruses wherein each virus differs in relation to other viruses of the plurality as to the amino acid sequence of the exterior protein, (2) isolating a virus that infected one of said host cells; and (3) administering the virus isolated in step (2) to a target cell so as to transfer the nonviral nucleic acid to the host cell, wherein prior to step (3) (preferably prior to step (1)) the nonviral nucleic acid sequence intended for delivery to a host cell is incorporated into a nucleic acid viral molecule of said virus. The target cell may be in an organism (e.g., a human or other mammal), in blood or other tissue outside an organism, or in cell culture (for example, either in liquid suspension or on solid surface). As in steps (1) and (2) of the method of isolating a virus, a cell selection marker may be used.

In another aspect, the invention is a retrovirus, said retrovirus created and isolated by a method of this invention.

A method for screening a viral display library for variants of a virus that target a known tissue-specific surface protein where the library is expressed on the surface of cells, said virus a library virus, and wherein the tissue-specific surface protein is expressed on the surface of a vector virus, said method comprises the steps of:

(1) administering a vector virus to a population of host cells, said vector virus expressing said tissue-specific protein on its surface, said host cells expressing a random library comprising a plurality of exterior proteins of said library virus, wherein the vector virus being administered comprises a nucleic acid molecule coding for a cell-selection marker and wherein the amino acid sequence of each exterior protein in the plurality differs from the amino acid sequence of other exterior proteins of the plurality; and (2) isolating a cell that bound to the tissue-specific surface protein on the vector virus being administered or isolating a library virus from said cell.

In another aspect applicable to all viruses, the invention is a method for screening a viral display library for viral variants that target a known tissue-specific surface protein where the library is expressed on the surface of cells, said virus a library virus, and the tissue-specific surface protein is expressed on the surface of a vector virus. The method comprises the steps of:

(1) administering a vector virus to a population of host cells, said virus (preferably a pseudotype, such that the tissue-specific surface protein is coded for by a nucleic acid molecule that is not part of the vector virus) expressing said tissue-specific protein on its surface, said host cells expressing a random library comprising a plurality (preferably more than $1 \times 10^5$, more preferably more than $1 \times 10^6$) of exterior proteins of said library virus wherein the vector virus being administered comprises a nucleic acid molecule coding for a cell-selection marker and wherein the amino acid sequence of each exterior protein in the plurality differs from the amino acid sequence of other exterior proteins of the plurality; and (2) isolating a cell that bound to the tissue-specific surface protein on the vector virus being administered or isolating a library virus from said cell. Preferably each cell expresses a small number of amino acid sequence variants of exterior viral proteins, the average number being less than 10, as close to 1 as possible.

For all libraries and all methods, one preferred embodiment is to include a coding region for a nonviral cell-binding peptide (an example is the CCR5-binding peptide discussed herein) in the viral exterior protein of interest, especially within the region that is varied for purposes of constructing the library.

In selecting a virus for delivery of a gene to a cell, it is clearly preferred to select a virus that does not have a pathologic effect on the host cell or host. Therefore, it is preferred to modify a nonhuman retrovirus for use as a vehicle into a human. However, recent advances indicate that lentiviral delivery vectors (such as those derived from the retrovirus HIV-1) have an advantage in that they infect non-dividing cells. Furthermore, Env proteins isolated using the procedures outlined here could be used to eventually pseudotype lentiviral particles or alphavirus particles.

It is preferred that the cell-selection marker, generally a protein, be a drug-resistance marker.

It is understood that a random display library can comprise two or more viruses which have the identical envelope protein amino acid sequence.

The libraries of the present invention, and therefore the related processes of making and using them, are useful as pools of viral vehicles from which an appropriate vehicle can be selected to transfer a gene to a host cell. A large number of possible applications exist for gene therapy vectors created using the present inventions. They can be used to target specific cell types for any gene therapy application. These include the correction of diseases that are caused by enzyme deficiencies such as diabetes. For example, the missing enzyme can be expressed from liver or muscle tissue. Selected Env variants can also be used to target genes to heart cells to deliver factors which promote tissue regeneration in diseased states. Delivery of toxic genes to tumors or virus-infected cells for therapeutic applications can also be accomplished. For lower organisms, such as microorganisms, the methods are applicable for modifying the host range of the viruses for purposes of either killing the microorganism or transferring beneficial genes.

BRIEF DESCRIPTION OF THE DRAWINGS

FIG. 2. Determinants of receptor specificity for amphotropic 4070A virus. The partial amino acid sequences of amphotropic 4070A Env VRA from residue 50 to 74 (SEQ ID NO:24) and VRB from 129 to 157 (SEQ ID NO:25) are shown, as is a partial Mo-MCF sequence (SEQ ID NO:27). Differences between amphotropic Env and Mo-MCF polytropic Env within VRA are shown below the amphotropic sequence. Hyphens denote the absence of residues. Substitution of amphotropic sequences by polytropic sequences within this region affects interaction with the amphotropic receptor (34). Regions affecting receptor binding when substituted by a VSV tag are underlined (9). (For VRA, the underlined sequence is SEQ ID NO:15; for VBS, the underlined sequence is SEQ ID NO:16). Y60 and V61 (bold) have been shown to be important for infection mediated by amphotropic/FeLV-B Env hybrids (86). Changes A69G, Q72K and V137M (bold) alter the host range from amphotropic to 10A1 (33).

FIG. 3. Determinants of receptor specificity for a C-subgroup feline leukemia virus. Shown are sequences of FeLV-A strain A/Glasgow (top) and FeLV-C strain C/FZ215 (middle) within the N-terminal portions of Vr1. Hyphens denote the absence of residues. Replacing the A/Glasgow sequence in this region by the C/FZ215 sequence switches the tropism of the virus from A to C (77). A portion of the VRA region of amphotropic 4070A Env is shown for comparison (bottom). (Sequence identifiers are as follows:

SEQ ID NO:17 for FeLV-A; SEQ ID NO:18 for FeLV C; and SEQ ID NO:19 for 4070A).

Figure 4:
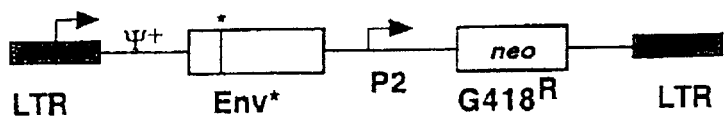
Figure 4:
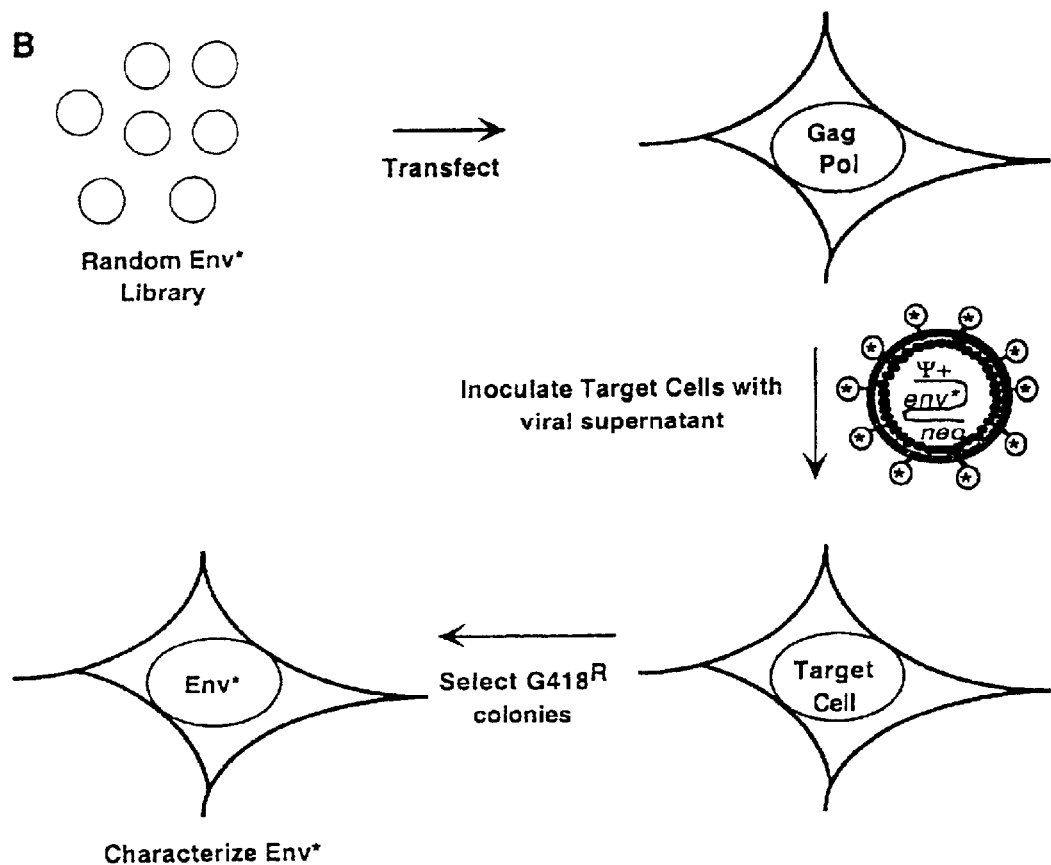

FIG. 4. Use of a random Env library to select Env proteins with novel targeting properties.
A) Schematic diagram of a retroviral vector expressing Env proteins containing random amino acid sequences within the receptor targeting site (Env*). The position of the random sequence is denoted by an asterisk. The Env* proteins are expressed from the retroviral LTR promoter. The G418 resistance gene is expressed from a second promoter (P2). The presence of the Ψ sequence allows the transcript to be packaged into a retrovirus.
B) In order to select Env* proteins capable of mediating binding and entry of cells to be targeted, a library of plasmids containing the construct shown in A are transfected into cells which express the retroviral core proteins Gag and Pol. Viral supernatants from these transfected cells are harvested and used to inoculate the cells to be targeted. If an Env* protein contains an amino acid sequence within its receptor targeting site which allows it to mediate viral entry, then a retroviral transcript containing that Env* variant gene will be transferred to the targeted cells and give rise to G418$^R$ colonies. The novel Env* gene can then be further characterized.

Figure 5:
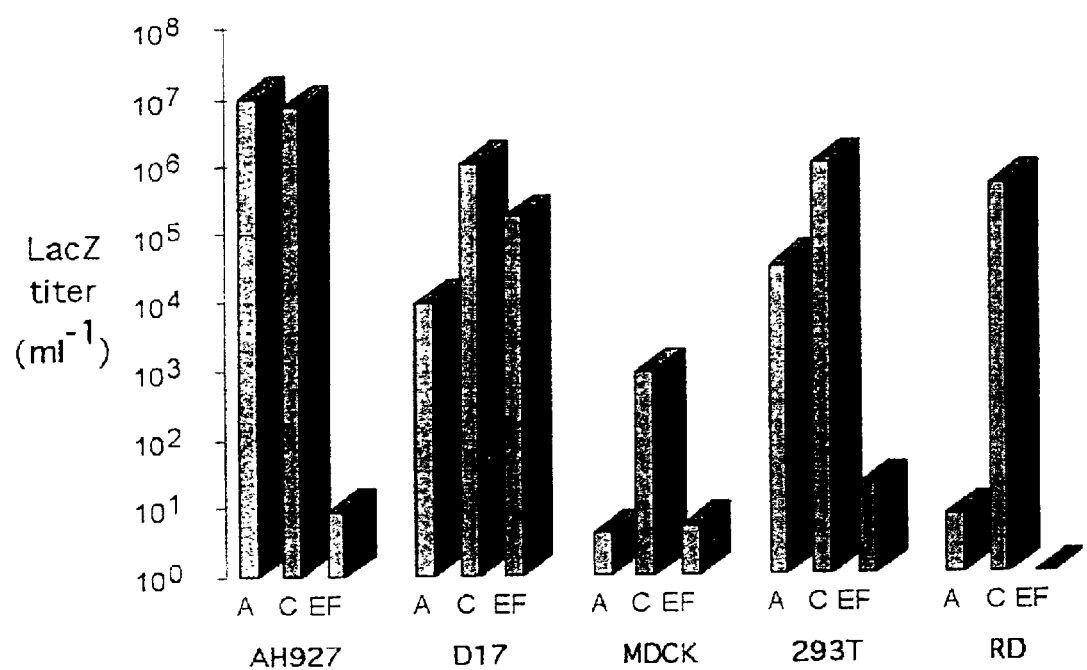

FIG. 5. Results of EF infection of various cell types.

FIG. 6. A sequence comparison of three receptor-determining regions. FeLV-A Env (top); FeLV-C Env substitutions which alter receptor usage (middle); locations of random amino acid substitutions in a library of FeLV Env variants (Sequence identifiers are as follows: SEQ ID NO:12 for the FeLV-A sequence; SEQ ID NO:13 for the C-subst sequence; SEQ ID NO:14 for Random sequence.).

Figure 7:
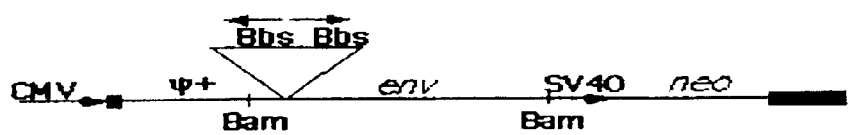

FIG. 7. Schematic diagram of a retroviral nucleic acid vector used for random insertion of amino acids.

FIG. 8. Example of site of variable insertion of nucleotides. The hybridization product of the three shown oligonucleotides is used as the insert into Bbs1-cut pRVL. N represents any nucleotide. (Sequence identifiers are as follows: SEQ ID NO:20 for the top sequence; SEQ ID NO: 21 for the lower sequence at the left; SEQ ID NO:22 for the lower sequence at the right.

Figure 9:
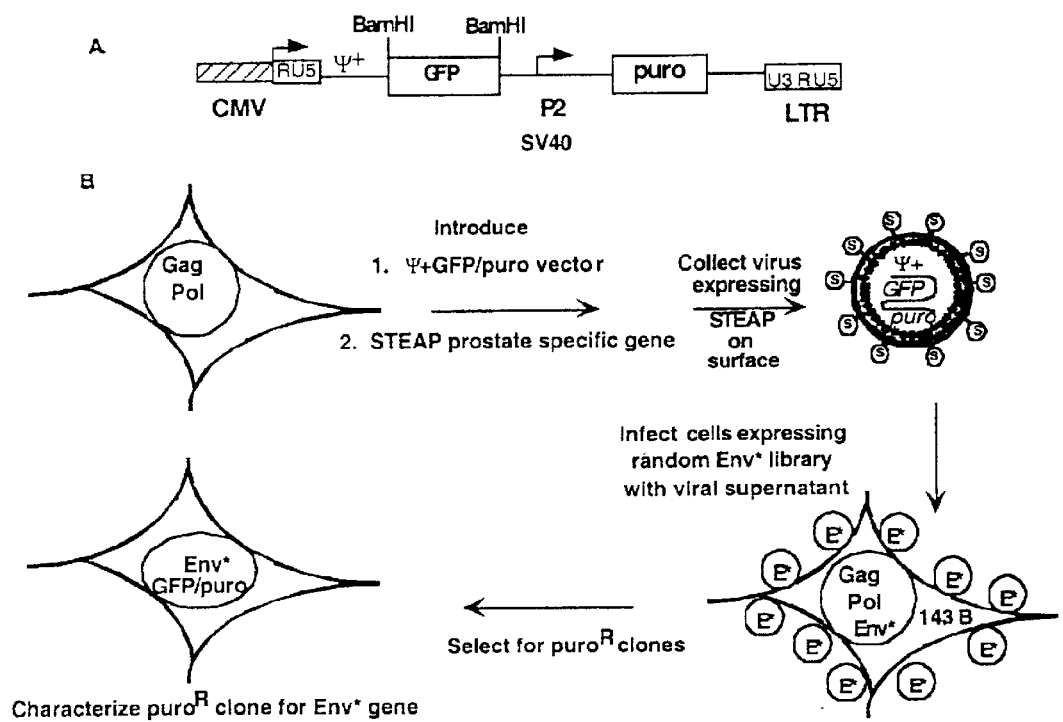

FIG. 9. An "inverse" targeting strategy for identifying prostate-specific Env proteins.

FIG. 10. The sequence of the VRA/Vr1 region of FeLV and a RANTES peptide sequence (underlined) flanked by random amino acids. (Sequence identifiers are SEQ ID NO:12 for the FeLV sequence; and SEQ ID NO:23 for the entire sequence in the lower line, and SEQ ID NO:26 for the underlined RANTES sequence.

Figure 11:
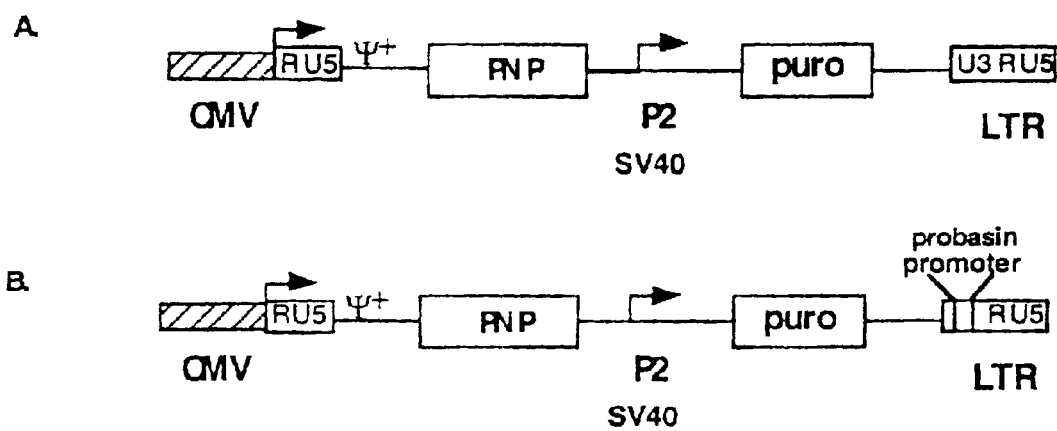

FIG. 11. Two Retroviral Cassettes. The expression of the cassette in part A is controlled by the MuLV LTR and can therefore be expressed in a number of tissues. The specificity of PNP expression will therefore be dependent on the prostate-specific Env protein used to transfer the vector. A second level of control can be added by inserting the probasin prostate-specific promoter (19) into the U3 region of the LTR as shown in part B.

Figure 12:
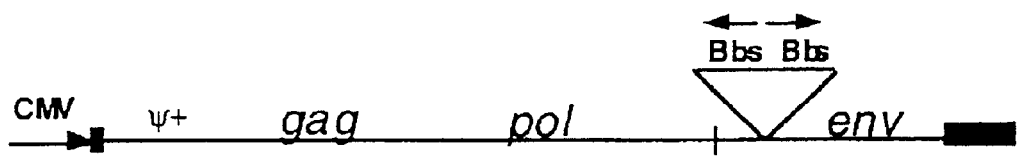

FIG. 12. Schematic drawing of a plasmid containing the gag and pol genes.

Figure 13:
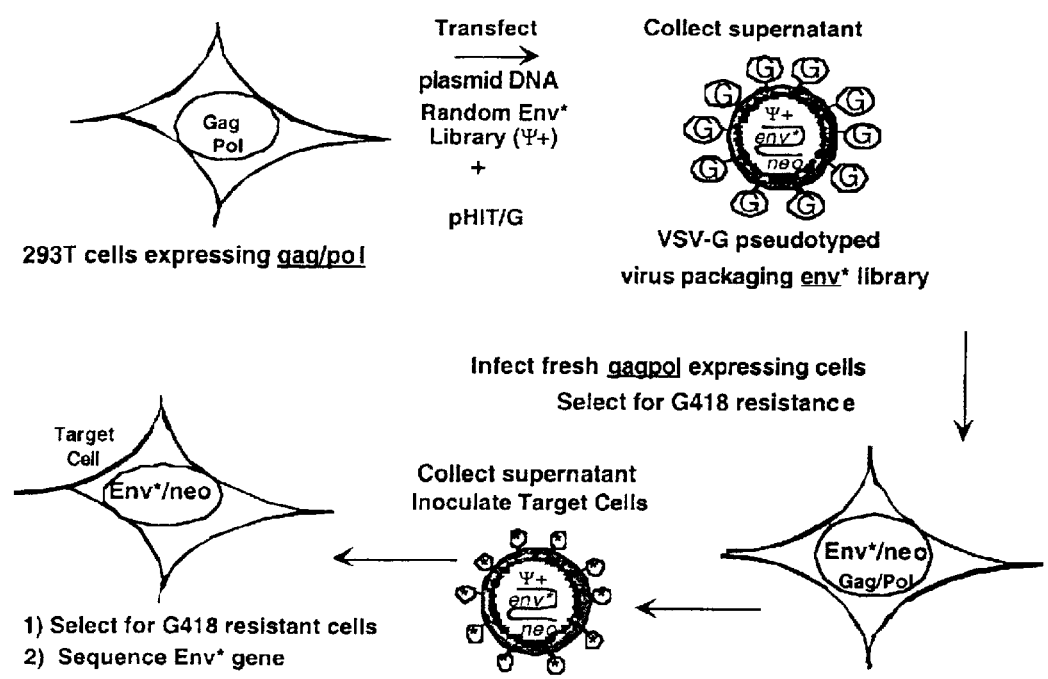

FIG. 13. Modified strategy for screening Env library with random substitution in the receptor determining region.

DETAILED DESCRIPTION OF THE INVENTION

A basic outline for a strategy underlying the present invention is depicted in FIG. 4. In this approach, the env genes containing random nucleotide sequences in the receptor targeting site (env*) are carried on a packageable retroviral cassette along with a drug resistance marker (FIG. 4A). First, plasmids containing this cassette are transfected into cells expressing retroviral core particles (FIG. 4B). Virions produced from these cells will express mutant Env* proteins on their surface and will carry the cassettes. Env* proteins which contain appropriate novel amino acid sequences will mediate binding and entry into the desired cell type. Incorporation of the cassette into the genome of the infected cell will lead to the acquisition of drug resistance. The Env* protein present within such a drug resistant clone can then be further characterized. This strategy thus allows the direct selection of fully functional novel Env proteins. Variations of this strategy are also possible. The goal of this strategy differs from that of using phage display to isolate novel antibodies with high affinity for specific ligands in that the Env protein does not simply supply a binding function.

One of the advantages of this approach over using a preselected ligand with known cell-binding properties is that it does not require a predetermined conformationally active orientation to fit onto the Env protein. It also does not necessarily entail foreknowledge of a cell-type specific receptor. The simplest although not the only way of randomizing sequences is to randomly substitute a single linear region of the Env molecule. Since the separate variable regions A and B both interact directly or indirectly with the receptor in both amphotropic and ecotropic Env, randomization of sequences would therefore be more effective in an Env molecule which contains minimal VRB sequences such as FeLV-A. The random library method entails minimal perturbation of the Env structure due to the precise substitution of the receptor binding domain by random amino acids. Using this technique, over one million different variant constructs can be screened at a time for gene transfer function.

The initial screening round described in this application identifies viable modified virus. A secondary screening is required to define tissue specificity. The use of the VSV-G to create a stable cell population producing the library should increase the complexity of the library available for testing (FIG. 13). This approach of substituting the Vr1 region may be adapted to other viruses, such as Rat Leukemia Virus, for which we have isolated an infectious isolate. The library of random viral Env proteins, such as FeLV Env proteins can also be pseudotyped onto other vectors, such as lentiviral vectors, for infection and screening of non-dividing cells and primary tissues.

Improvements in the entry properties of a selected virus with a novel binding site should also be achievable by passage of the virus in culture.

Abbreviations and Glossary

A "coding region" of a nucleic acid for a designated protein refers to a region in an mRNA molecule that contains the base sequence which is translated into an amino acid sequence. It also covers any DNA or RNA sequence that is complementary to such an mRNA sequence. Additionally, "coding region" covers any DNA sequence that is the same as such an mRNA sequence (except that T is used in place of U) and, in the case of a DNA sequence that alternates introns with exons so that the sequence can be processed to make an mRNA molecule, "coding region" covers the group of coding exons that determines the amino acid coding region of the mRNA molecule.

An "exterior protein" of a virus is one that is on the exterior of the virus and is preferably one that contacts a cell receptor as part of the virus's infection process for that cell.

FeLV: Feline leukemia virus

Amphotropic 4070A: A strain of amphotropic murine leukemia virus.

MuLV: Murine leukemia virus.

Mo-MuLV: Moloney MuLV

RaLV: Rat Leukemia virus.

"The receptor binding domain" is the region of Env protein that is involved directly or indirectly in cell receptor contacts. Three variable regions with the receptor binding domain are the VRA, VRB, and VRC regions.

Retrovirus (also known as retroviridae) is the taxonomic name for a family of RNA-containing viruses that have a reverse transcriptase. Their genome can be transcribed to DNA, which can be incorporated into a host cell's genome.

Figure 1:
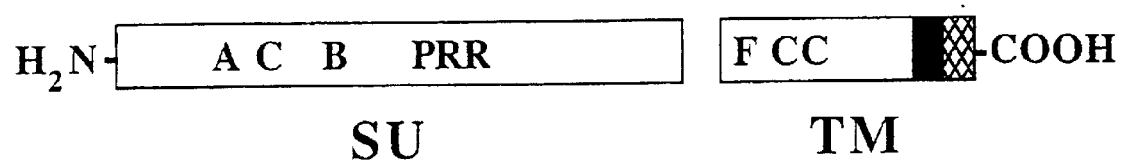
FIG. 1. Linear structure of the MuLV Env proteins. The surface (SU) and transmembrane (TM) proteins are indicated. Variable regions A, B and C are labeled as well as the proline-rich region (PRR) within SU. The putative fusion peptide (F) and the coiled-coil (CC) region are indicated within the TM. The membrane spanning portion of the TM is shaded. The cytoplasmic domain is cross-hatched. For Fr-MuLV, SU is 445 amino acids long and TM is 200 amino acids long.

The viral "Env" protein consists of two proteins, the Surface (SU) and Transmembrane (TM) proteins which are cleaved from a common precursor (FIG. 1). Extensive analyses have localized the receptor binding domain to the N-terminal half of the SU protein (5, 6, 7, 8, 21, 35, 38, 67, 70). This is followed by a proline rich region (PRR), which is proposed to behave either as a hinge or trigger to communicate receptor binding to the fusion machinery (30). The C-terminus of the SU is highly conserved and interacts with the TM protein (65, 71). TM contains the fusion peptide (F) and a coiled-coil region (CC), analogous to that found in influenza HA (28), followed by the transmembrane and cytoplasmic domains.

A "library" is a collection of viruses, proteins, or nucleic acid molecules. A "display library" is a library wherein the variable viral proteins are on the exterior of the virus and are therefore "displayed."

A "plurality" is two or more unless otherwise specified.

A "cell selection marker" is a protein the expression of which distinguishes the cell from other cells which do not express the protein. Such a cell selection marker can confer the ability to survive, for example in a specific medium, or can cause a change in the cell's environment or properties such that expression of the marker can be detected by observation or measurement. For example changes in the cell's medium or in the cell's binding properties may occur. Other aspects of the cell's behavior or its physical parameters may be changed by expression of the cell selection marker. Any of these changes enable the expressing cells to be detected and separated from nonexpressing cells by known methods.

A preferred cell selection marker is a protein that provides a cell with the means to survive or divide under conditions where cells without the marker cannot. An example is a drug resistance marker. Other cell selection markers include enzymatic markers whose expression causes an event detectable by observation or by known methods such as OD measurement or ELISA, such as a color change, or light production. Cells expressing such markers can be separated from nonexpressing cells by conventional cell sorting techniques (see for example Fiering et al. (1991) Cytometry 12(4):291–301); Meyer et al. (1998) Diabetes 47:1974–1977), and by fluoresence microscopy, in combination with standard tissue culture cloning techniques such as cloning rings and clonal dilution. Other cell selection markers include proteins whose expression on the cell's surface can be used to separate expressing cells from nonexpressing cells. An example is a single chain antibody which binds to hapten-coated magnetic beads which beads can be used to separate expressing cells from nonexpressing cells (see for example Chesnut et al., (1996) J. Immunol. Methods 193(1):17–27). Another example is a cell surface marker that can be detected using a fluorescence-tagged molecule (such as an antibody). The cells which express the molecule may be fluorescently labeled and separated from the nonexpressing cells by known techniques such as FACS (fluorescence activated cell sorting).

Thus for example the neo gene in the library of FIG. 4A can be replaced by any cell selection marker described above allowing the identification and purification of cells that have been transduced with an Env* variant from the random library. Examples of such markers are β-galactosidase, GFP (green fluorescent protein), a membrane-bound single chain antibody, or any other detectable cell surface marker.

Preferred Regions for Amino Acid Substitutions

Preferred Regions for Amino Acid Substitutions

Table 1 shows the envelope protein regions most likely to be responsible for interactions between retroviral Env and its receptor. The data in that Table are based on an examination of published results. These regions are the preferred regions for amino acid variation in the display library. However, it is important to note that our assay for successful variation of an envelope protein does not just reflect the ability of the Env protein to bind to a target cell but also whether subsequent interactions with the host cell lead to virus-cell fusion and formation of the retroviral preintegrative complex so that its nucleic acid is stably copied into the host cell genome.

Amino Acid Sequences of Variable Regions for Mo-MuLV, 4070 Amphotropic Virus, FeLV-A, and RaLV The Amino acid numbers refer to the sequence of the mature protein (i.e.-signal peptide removed).

Mo-MuLV

VRA: residues 51–115

HGPSYWGLEYQSPFSSPPGP-
    PCCSGGSSPGCSRDCEEPLTSLTPRCN-
    TAWNRLKLDQT

THKSNEG (SEQ ID NO:1)

VRB: residues 169–179

SDQAVQVCKDN (SEQ ID NO:2)

VRC: residues 122–130

PHRPRESKS (SEQ ID NO:3)

REF: Shinnick, T. M., R. A. Lerner, and J. G. Sutcliffe (1981) Nucleotide sequence of Moloney murine leukemia virus. Nature 293: 543–548

4070A Amphotropic

VRA: residues 50–78

EEWDPSDQEPYVGYGCKYPAGRQRTRTFD (SEQ ID NO:4)

VRB: residues 129–158

PWDTGCSKVACGPCYDLSKVSNSFQGATRG (SEQ ID NO:5)

VRC: residues 85–90

HTVKSG (SEQ ID NO:6)

REF: Ott, D., R. Friedrich and A. Rein (1990) Sequence analysis of amphotropic and 10A1 murine leukemia viruses: close relationship mink cell focus-inducing viruses. J. Virol. 30:157–165.

FeLV-A (F6A)

VRA: residues 50–88

DTWEPIVLNPTNVKH-
    GARYSSSKYGCKTTDRKKQQQTYP (SEQ ID NO:7)

VRB: residues 144–149

QDNSCE (SEQ ID NO:8)

VRC: residues 95–105

HAPSLGPKGTH (SEQ ID NO:9)
REF: Donahue, P. R., E. A. Hoover, G. A. Beltz, N. Riedel, V. M. Hirsch, J. Overbaugh and J. I. Mullins (1988) Strong sequence conservation among horizontally transmissible, minimally pathogenic feline leukemia viruses. J. Virol. 63: 722–731.
RaLV
VRA:residues 61–81
DSWEHTERTPHNSYPPCRHSD (SEQ ID NO:10)
VRB:residue 130–132
PGE
VRC:residues 88–93
GKRTRE (SEQ ID NO:11)
REF:Lee, S.-Y., T. M. Howard and S. Rasheed (1998) Genetic analysis of the rat leukemia virus: Influence of viral sequences in transduction of the c-ras proto-oncogene and expression of its transforming activity J. Virol. 72: 9906–9917.

Construction of a Vector with a Gene Toxic for Prostate Cancer Cells

Retroviral gene delivery cassettes can be constructed to deliver a suicide gene to prostate cells using the prostate-specific Env proteins derived from a random library. The *E. coli* purine nucleoside phosphorylase (PNP) gene serves as the suicide gene. When treated with 6-methylpurine-deoxyriboside, cells expressing PNP convert the prodrug to the highly toxic 6-methyl purine. This toxic compound is capable of killing not only cells expressing PNP but also bystander cells. Bystander cell killing using this approach has been reported to diagrammed in FIG. 11 are derived from the GFP/puro construct diagrammed in FIG. 9. The PNP gene replaces the GFP gene. Puromycin selection will be useful in determining the vector titer as well as selecting a homogeneous population of cells expressing PNP. This population will be useful in determining the extent of bystander cell killing by performing mixing experiments with cells not expressing PNP.

The expression of the cassette in part A is controlled by the MuLV LTR and can therefore be expressed in a number of tissues. The specificity of PNP expression will therefore be dependent on the prostate-specific Env protein used to transfer the vector. A second level of control could be added by inserting a tissue-specific promoter such as the probasin prostate-specific promoter (19) into the U3 region of the LTR as shown in part B. Upon replication of the cassette and integration into the host cell genome, the probasin promoter becomes located upstream of the PNP gene (the CMV promoter is not packaged into the cassette). The PNP gene will therefore be expressed specifically in prostate cells in an androgen dependent fashion. Although use of the probasin promoter has the advantage of added prostate specificity, there are disadvantages which make the unmodified LTR a useful alternative. One is that genes expressed from retroviral vectors employing tissue specific control elements are sometimes not as highly expressed as when controlled by an LTR (20). The other disadvantage is that the prostate-specific promoters characterized to date are androgen dependent. Since treatment of prostate cancer can involve anti-androgen strategies, a suicide gene under androgen dependent gene control will not be beneficial for such patients. Tumors that lose their androgen dependence could also prove refractory to androgen-dependent suicide gene therapy. Each type of vector may therefore have its own specific application.

Therapeutic Aspects of the Invention

Therapeutic preparations of the viruses of the invention include those utilizing pharmaceutically acceptable carriers, or other adjuvants as needed, and are prepared in effective dosage ranges as needed. The route of administration is one that allows the virus to reach its target cell or cells.

Appropriate dosage levels will depend on the patient and the therapeutic purpose. Over Appropriate dosage levels will depend on the patient and the therapeutic purpose. Over time intervals, increasing amounts of virus can be administered, each administration followed by an assay (e.g., assays for tumor mass or cell count; hybridization assays of selected biopsy samples for the retroviral genes; assays for enzyme products or the enzyme where the gene for an enzyme is delivered) to determine if sufficient number of target cells have been successfully transfected.

EXAMPLES

The following examples are intended to illustrate the invention, not limit it.

Example 1

For the purposes of creating a random display library we have used the subgroup A feline leukemia virus envelope (FeLV-A Env). (Donahue, P. R., Hoover, E. A., Beltz, G. A., Riedel, N., Hirsch, V. M., Overbaugh, J. and Mullins, J. I. (1988) Strong sequence conservation among horizontally transmissible, minimally pathogenic feline leukemia viruses. J. Virol. 62:722–731.) FeLV-A Env has advantages over other retroviral Envelope proteins that have been the subject of other retargeting studies. First, the FeLV-A Env receptor-binding domain is a much simpler structure. Second, its receptor-determining region has been well characterized and shown to consist of a short stretch of amino acids. This sequence (shown in FIG. 3) can easily be replaced with random amino acids to create a library. The Env expression vector that we are currently using is shown in FIG. 7. (Plasmid 61E encoding the replication-competent A subgroup virus, the Env used to create the random library, is available from the National Institutes of Health NIAID AIDS Reagent Program.) The most important feature of this construct is that the env gene is contained on the same packageable retroviral cassette as a drug selectable marker. Thus, if a given env gene is functional, it will be transferred to the targeted cell along with the drug resistance marker. The functional variant sequence can then be characterized by PCR amplification of the infected cell DNA.

Studies on FeLV have shown that the host-range of the virus can be changed from type A to type C through exchange of a limited region, termed Vr1 or VRA. A sequence comparison of these receptor-determining regions is shown in FIG. 6. The top line of FIG. 6 shows the wild-type FeLV-A Env sequence into which random substitutions will be made. Hyphens denote gaps in the representation of a sequence but not the actual sequence. The second line shows the sequence changes which redirect the A subgroup virus to the C subgroup receptor. The third line shows the positions where we have made random amino acid substitutions in the sequence (X is any amino acid). In order to create this library, we have created a vector which can be modified for the insertion of any short sequence within the env gene. The vector (pRVL, shown in FIG. 7) is based on pHIT111 (4). It is flanked by LTR sequences vector (pRVL, shown in FIG. 7) is based on pHIT111 (4). It is flanked by LTR sequences (black boxes) and contains a retroviral packaging signal (Ψ). The env gene contains an engineered back-to-back pair of BbsI restriction sites which allows the sites to be precisely cut out and replaced by hybridized oligonucleotides which encode random amino acids within the appropriate context. The oligonucleotide combination which we have used to create the randomized amino acid sequence is shown in FIG. 8. This type of oligonucleotide hybrid is patterned on hybrids used to create random phage display libraries (10). The short oligonucleotides are added to the longer, randomized nucleotide in a 10:1 molar ratio (short:long). The mixture is boiled briefly and cooled slowly to room temperature. The over-hanging ends produced as a result of BbsI cutting are not overlapping and therefore the cut vector will not religate. If a singly cut vector religates, or if an intact vector remains in the ligation mix, it will result in a truncated protein due to the presence of a stop codon between the BbsI sites. Use of high concentration ligase (New England Biolabs) and electroporation (Bio Rad) into ElectroMAX DH10B high efficiency competent cells (Source: Gibco/BRL) has allowed us to create a library containing $1.0 \times 10^6$ different random sequences. (For electroporation see Calvin NM and Hanawalt PC (1988) J. Bacteriol. V. 170, p. 2796ff; Dower, William J. et al (1988) Nucl. Acid Research v. 16, p.6127ff). By increasing the amount of DNA in the ligation by a factor of 10 (from about 1 microgram to about 10 micrograms) we have increased the number of random sequences to over $10^7$.

The design of pRVL provides a simple means to substitute different sequences into the receptor determining region or alter the position of the random sequences. The BamHI sites shown in FIG. 7 are unique in the plasmid. New BbsI sites can therefore be created at any position using overlapping PCR. The BbsI cut site is separate from the recognition site. Therefore, coding sequence can be maintained; regardless of how the restriction sites are placed. The end primers can include BamHI linkers attached to 5' and 3' Env sequences. The overlap primers can contain the back to back BbsI sites placed appropriately for a given randomized oligonucleotide.

Our initial strategy (see FIG. 4) has been successfully developed. With this method, the FeLV env library is transfected into the 293T cell line along with a plasmid that expresses the retroviral gag and pol genes (pHIT60)(4). A 293T cell line stably expressing Gag and Pol (from plasmid CeB) can also be used. (See Example 2.) The 293T cell line expresses the SV40 T antigen. This allows amplification of the transfected plasmids that contain SV40 origins of replication. Inoculation of acceptor cells expressing gag and pol with virus-containing supernatant from the transfected cells is then followed by selection for G418 drug resistance. The presence of Gag and Pol in the acceptor cell population allows further characterization of the Env variant which has been transferred. This allows initial screening of the variant for its cell-type specificity.

100 micrograms of each plasmid pHIT60 and a library plasmid preparation was used to transfect ten 10 cm dishes of 293T cells by calcium phosphate. The library contained $10^6$ different random sequences. Supernatant from the ten 10 cm dishes of 293T cells was then used to inoculate AH927 feline fibroblasts expressing Gag and Pol. Three $G418^R$ colonies were obtained. Supernatant from the cells of one of those colonies was capable of transferring G418 resistance to fresh AH927 cells. The FeLV variant from this clone was termed EF. This clone was further found to have an altered host range relative to related FeLV Env proteins. In order to quantitate infectivity of retroviral particles expressing various Env proteins on their surface, TELCeB6 cells (Ref. #12, Institute of Cancer Research (London)) were used. A plasmid encoding Blasticidin S resistance can be obtained from Invitrogen (pcDNA6/TR). This is the drug selection marker on the CeB plasmid. TE671 cells are the base cell line from which TELCeB6 cells were derived (TE671 cells are available from ATCC). TELCeB6 cells express the retroviral core proteins Gag and Pol as well as a transferable retroviral cassette carrying the lacZ gene coding for β-galactosidase. Counting the number of blue LacZ expressing acceptor cells after X-Gal staining allows simple quantitation of infectivity (Claudio Peredo, Lucille O'Reilly, Kim Gray and Monica Roth (1996) J. Virol. 70; 3142–3152).

The data discussed below indicate that:

(1) High titers of EF ($>10^5$ $ml^{-1}$) can be obtained on D17 cells(Source: ATCC); and (2) The receptor usage of EF on D17 cells is more similar to the C subgroup FeLV than the parental A subgroup FeLV. (For C Subgroup FeLV, see Riedel, N., Hoover, E. A., Gasper, P. W., Nicolson, M. O., Mullins, J. I. (1986) Molecular analysis and pathogenesis of the feline aplastic anemia retrovirus, feline leukemia virus C.

Although the C subgroup FeLV has a broad host range, EF shows very highly specific infection of D17 canine osteosarcoma cells. be obtained at a titer of $>10^5$ $ml^{-1}$ from TELCeB6 cells expressing EF Env. Titers on all other cell lines are near background (close to zero). Titers were determined by endpoint dilution in 35 mm dishes with 2 mm grids. The MDCK cell line is a canine kidney cell line. (Source: American Type Culture Collection). The four orders of magnitude difference in titer between the canine osteosarcoma and canine kidney cell lines suggests that random display Envelope libraries could be successfully applied to tissue-specific targeting. The C subgroup FeLV Env from TELCeB6 viral producer cells mediates infection of AH927 cells (regarding AH927 cells, see Riedel, N., Hoover, E. A., Dornsife, R. E., and J. I. Mullins (1988), Pathogenic and host range determinants of the feline a plastic anemic retrovirus. Proc. Natl. Academy of Science USA 85, 2758–2762), D17 cells, 293T cells, and RD cells with titers close to or greater than $10^6$ $ml^{-1}$. Infection of MDCK cells mediated by C Env was lower at approximately $10^3$ $ml^{-1}$. The parental A subgroup Env infects AH927 cells with a titer of $1.0\times10^7$ $ml^{-1}$. Infection of D17 and 293T cells by A was moderate and infection of RD and MDCK cells was close to background levels. Substitution of the receptor-determining region of FeLV-A Env by the corresponding region of EF indicated that the change in cellular tropism was determined solely by the ten "random" amino acids of EF (not shown).

In order to determine which receptor was used by the EF Env on D17 cells, interference assays were performed. D17 cells expressing either the A subgroup Env or the C subgroup Env were tested for the ability of EF to infect them. Cellular expression of an Env protein results in the downregulation of the receptor utilized by that Env protein thus preventing further infection via that receptor. A 99% decrease in titer is generally considered to be indicative of interference. The first column of Table 2 shows the titer on D17 cells using supernatants from the TELCeB6 populations listed at the left. The next two columns indicate the titers expressed when the same supernatants were used to infect D17 cells expressing either an A Env or a C Env, respectively. Those titers as a percentage of titers on D17 cells not expressing an Env protein are shown in parentheses. The data indicate that A subgroup Env expression prevents further infection by A Env-bearing particles. C Env expression prevents further infection by C Env-bearing particles. C Env expression also inhibits infection by A Env-bearing particles. These data suggest that C Env uses both the A Env receptor and a C Env-specific receptor but A Env does not use the C Env-specific receptor since A Env expression does not interfere with C virus infection. Since EF infection is since A Env expression does not interfere with C virus infection. Since EF infection is inhibited on C Env-expressing D17 cells but not on A Env-expressing cells, EF receptor usage has been altered from the A parental pattern to the C pattern. Further experiments can determine whether EF Env expression interferes with C or A infection. Such experiments can indicate whether EF uses only the C-specific receptor or both the C-specific and the A receptor. Although the receptor usage by EF on D17 cells is similar to the C subgroup receptor usage, the fact that the cellular tropism of C and EF are quite distinct indicates that the receptor binding and entry properties of EF do not simply mirror those of the C subgroup.

Example 2

A modified strategy is described in FIG. 13. This strategy should enable a more thorough screening of a random Env library. Instead of using a transient expression system to create the viral supernatant, a cell population stably expressing the library of virus particles is created. This provides a long term source for the viruses to be screened and also increases the total quantity of each individual virus derivative—enhancing its likelihood of being identified for a given target cell.

First, a stable cell population which constitutively produces retroviral particles incorporating recombinant Env* proteins onto their surfaces is constructed. Cotransfection of the Env* library plasmids along with a plasmid (pHIT-G (11)) expressing the VSV-G protein into a gag-pol producing 293TCeB cell line results in the transient production of retroviral particles pseudotyped with the VSV-G protein and carrying the random-substituted retroviral cassettes. We have created the cell line by transfection of the CeB plasmid (12) into 293T cells and selecting for Blasticidin S resistance. (For 293T cells, see DuBridge, R. D., P. Tang, H. C. Hsia, P.-M. Leong, J. H. Miller and M. P. Calos (1987) Mol. Cell. Biol. 7:379–387; Pear, W. S., G. P. Nolan, M. L. Scott, and D. Baltimore (1993) Proc. Natl. Acad. Sci. USA 90: 8392–8396.) Both the G protein-expressing plasmid and the library plasmids contain SV40 origins of replication and are amplified by the SV40 T antigen in the 293T cells. Use of the wild-type FeLV-A Env (Donahue et al., above; NIAID AIDS Reagent Repository) in place of the VSV-G protein yields a titer of $10^4$ transducing particles per ml of supernatant on AH927 feline fibroblasts. (Riedel et al., above). Use of the pHIT/G plasmid expressing the VSV-G protein to infect 143B cells should increase that yield by at least one to two orders of magnitude. It also provides a stable cell population constitutively producing a supernatant with particles incorporating Env* proteins as a long term source of the library. Inoculation of FeLV Env* pseudotyped viral particles into fresh gag/pol producing human cells (143B) with that supernatant, followed by selection for G418 resistance (as a result of the presence of the neo cell selection marker) will lead to the production of a population of cells stably producing, in this supernatant, retroviral particles incorporating the recombinant Env* proteins on their surface and carrying the cassette encoding the corresponding surface Env* protein. We have constructed a 143Bgagpol line for that purpose by stably transfecting the gag/pol expressing plasmid CeB (12) into 143B cells and selecting for Blasticidin S resistance. The use of human cells (such as 293T) in these procedures diminishes the possibility of obtaining recombinant repair products between the FeLV env sequences and endogenous retroviral sequences.

By this method stable cell lines expressing libraries of retroviral particles containing random amino acid substitutions in the Env protein were created with complexities as high as $3 \times 10^6$ and have been maintained for at least 10 cell doublings. Selection for Env variants on a particular cell-type led to the identification of variants that are specific for that cell-type. Using this random library screening technique, Env variants were obtained that are specific for human cells.

Thus, constitutive libraries were created of several complexities ranging from $8 \times 10^4$ to $3 \times 10^6$. These libraries were created using the strategy diagrammed in FIG. 13 and as described above. One clone (C82) that was obtained from screening the library of $8 \times 10^4$ complexity on D17 cells has been shown to specifically infect D17 cells with a titer of $2.5 \times 10^4$ lacZ colony forming units per ml. Levels of less than 10 c.f.u. per ml were observed on AH927, MDCK, 293T and RD cells.

Another Env protein was selected from a constitutive retroviral producer cell line of $3 \times 10^5$ complexity. This Env protein (LI) was selected on 143B human cells, giving a titer of $3.8 \times 10^3$ on those cells. An even higher titer ($2.8 \times 10^5$) was observed on human 293T cells. Titers close to background were obtained on AH927 feline fibroblasts, D17 canine osteosarcoma, human RD and human TE671 cells.

Example 3

There is a low level (1 in $10^5$ viral integrants) of background gene transfer which is observed even in the absence of an Env protein on the surface of a gene-transducing virus. Our initial strategies therefore use acceptor cells expressing the viral Gag and Pol structural proteins to help distinguish drug resistant colonies containing bona fide functional Env variants from non-functional background.

In order to circumvent the necessity of creating Gag/Pol-expressing acceptor cells, the random Env library can be constructed in a replication competent retroviral vector which packages the gag and pol genes along with the random sequence-containing env gene. (Shown in FIG. 12). Since the creation of a random library requires a unique BbsI site in the plasmid for insertion of a random oligonucleotide, this basically entails eliminating the BbsI restriction enzyme sites from the gag and pol genes. Elimination of the BbsI sites (gag and pol genes) can be carried out using overlapping PCR mutagenesis (Ho, S. N., H. D. Hunt, R. M. Horton, J. K. Pullen, L. R. Pease (1989) Site-directed mutagenesis by overlap extension using the polymerase chain reaction. Gene 77: 51–59). A single point mutation that maintains the coding sequence of the viral protein would be sufficient.

The screening strategy would be similar to the strategy shown in FIG. 13. Since the library of plasmids encoding the random Env library also encodes the Gag and Pol proteins (shown in FIG. 12), the 293T cells do not have to express Gag and Pol. Also, since there is no selectable marker on this type of proviral construct, no selection can be used at any step. Instead, the VSV G protein is used to mediate infection of the cells to be targeted after concentration of the viral supernatant by centrifugation followed by filtration to remove donor cells. This allows all the Env variants to be stably incorporated into the target cell population. Cells are then passed normally, being sure to maintain adequate numbers to maintain the library. The cells are passaged normally for approximately one month or longer. During this time, functional Env variants will spread through the culture of targeted cells. After a sufficient time has elapsed, supernatant from the culture can be harvested, filtered and used to inoculate a fresh target cell population. Successful infection of the fresh target cell population can be assessed by measuring the release of reverse transcriptase into the supernatant. If a functional Env variant is present, reverse transcriptase activity should be detected within one to two weeks.

Once identified, the cell-specific Env variant can then be separated from the rest of the retro viral backbone and used to pseudotype retroviral gene delivery particles from any of the several gene packaging systems currently available.

Example 4

The purpose of this example is develop retroviral vectors which specifically target entry into prostate cells. The idea is to introduce a gene into the tumor cells which leads to their destruction. These can be genes involved in the immune response (18), or genes coding for prodrug converting enzymes (2,3). A critical aspect of this strategy is the specific targeting of the gene to the tumor cells, since delivery of the therapeutic gene to non-tumor cells could lead to undesirable side effects.

The goal is to alter the binding properties of the retroviral surface glycoprotein such that it binds to a protein specific to prostate cells, such as six transmembrane epithelial antigen of the prostate (STEAP). Two related approaches are described. The first approach is to screen a library of Env proteins containing short random oligopeptide sequences substituted into the receptor binding domain. The second approach is to directly target the virus to the STEAP on the surface of STEAP-pseudotyped retroviral particles. The advantages of these approaches are that the structure of Env is only minimally perturbed.

The supernatant from the cells producing retroviral particles with recombinant Env* on their surface (from Example 2) can be tested for the presence of novel Env* proteins capable of mediating entry into acceptor cells, including prostate cells such as PC-3, CA-HPV-10, PZ-HPV-7, LNCaP.FGC or DU 145. If the Env* protein mediates entry into the target cell, the G418 resistance will be transferred. The attached env* gene can then be sequenced from a PCR product of genomic DNA using appropriate primers. To confirm that the transfer of G418 resistance is linked to the env gene, the resultant G418 resistant colonies are further analyzed. The acceptor cells can be transfected with a gag/pol expressing plasmid; the titers of the resulting Env* pseudotyped particles should be significantly above background values. Testing the functional Env* protein for its ability to mediate transduction of other human cell types gives a measure of its specificity. RD, 293T, 143B, and TELCeB6 cells are examples of cells than can be tested. (Source of RD cells: ATCC of 143 B cell ATCC.)

Passage of the Virus to Increase Titer

Increases in the titers of the selected Env* proteins can be obtained by further passage in culture. We have already used serial passage in culture to obtain second site mutations in chimeric Env proteins with increased viral titer (17). To increase the titers of the prostate-targeted Env* proteins, the cassette encoding the selected Env* gene can be passed through a prostate or PSA-expressing cell line expressing gag and pol. The error-prone reverse transcriptase can create mutations in the Env* protein. Mutations which increase the functionality of Env* can be propagated through the culture at an increased rate and eventually dominate the population. The env* genes thus derived can be used further to develop vectors for delivering toxic genes to prostate tumors. These vectors can also include tissue specific promoters which restrict gene expression to the prostate tumor. The vectors can then be used as an adjunct to prostate cancer therapies such as surgery, chemotherapy and hormonal therapy.

Example 5

Inverse Screening of a Random Env Library for Variants Mediating Infection via Prostate-specific Membrane Proteins In order to target a specific tissue, advantage can be taken of the fact that a number of tissue-specific surface proteins have already been identified In addition to screening cells and tissues for novel retroviral envelope tropisms, one can screen the envelope library for variants that target these tissue-specific surface proteins. This can be accomplished using an "inverse" targeting approach where the locations of the tissue-specific surface protein and Envelope proteins are reversed: The envelope library is expressed on the surface of cells and the tissue-specific protein is expressed on the surface of a retroviral vector. The ability of an envelope and receptor to be reversed in this fashion has been previously demonstrated (25,26).

An advantage of targeting the Env protein to a previously identified prostate-specific protein is that the amount of effort required to screen for bona fide prostate-specific Env proteins is greatly reduced compared with a direct screen on prostate cells for entry via any proteins is greatly reduced compared with a direct screen on prostate cells for entry via any protein expressed on the cell surface. Recently, a cDNA encoding a prostate-specific multiple membrane passage protein termed STEAP has been identified which could serve as a target receptor (23). STEAP is highly expressed in advanced metastatic prostate tumor tissue and its expression is androgen independent. Most retroviral receptors identified to date, including those for MuLV or FeLV, are multiple membrane passage proteins, although receptors such as for the avian leukosis virus family are single membrane passage proteins. Targeting an Env protein to a multiple membrane passage protein specific to prostate tumors may be advantageous and provide the required geometry for effective viral entry. Another prostate-specific membrane protein that could be targeted using this strategy is the prostate-specific membrane antigen (PSM) (24).

In order to screen Env variants for the use of STEAP as a receptor, a modified, inverse strategy for library screening is proposed. The strategy is outlined in FIG. 9. It is called an "inverse" strategy because the locations of the Env proteins and the receptor have been reversed. The library of Env proteins is expressed on the surface of acceptor cells and the targeted receptor (STEAP) is expressed on the surface of the virion. The ability of receptor-pseudotyped retroviral particles to infect cells expressing the cognate Env protein has been previously demonstrated (25, 26). This has been effective for murine, human, and avian retroviruses and should therefore be effective with the FeLV env system.

Panel A shows a modification of the vector that was previously used to express the env* genes. In the modified version, the first gene expressed is green fluorescent protein (GFP) and the second gene expressed is one for a cell selection marker, the puromycin resistance (puro) gene. This vector contains the MuLV based packaging signal ($\Psi+$) plus all the cis-acting elements required for viral replication and thus can be incorporated into viral particles. This construct will be cotransfected along with a STEAP expression vector into TE671 cells expressing the gag and pol genes of MuLV (from plasmid CeB). The STEAP expression vector is a derivative of pHIT123 (22) which will express an human STEAP tagged with an HA (hemagglutinin) epitope from the cytomegalovirus (CMV) promoter. Puromycin resistant clones expressing the highest levels of the vector cassette can be identified using flow cytometric analysis for green fluorescent protein (GFP) expression. Expression of STEAP on the cell surface and on viral particles can be examined by Western blot analysis. stable library of cells expressing the Env* proteins. This library of cells is diagrammed in FIG. 9. If the library encodes a random sequence which permits Env to bind the STEAP protein and mediate entry of the virus into the cells, the vector DNA will be replicated and stably integrated into the target cell genome by the viral integrase protein. These cells can be identified by selection for growth in the presence of puromycin. A rapid test to confirm the specificity of such an Env* variant for STEAP is used to examine whether the GFP from the puromycin resistant clone can be transferred to cells expressing STEAP but not those which do not express STEAP. The chromosomal DNA from these clones is then isolated and the region encoding the Env* gene is amplified by PCR. The sequence of the random insert with the FeLV Env is determined using primers upstream and downstream of Vr1.

Inverse targeting has the benefit that the screening is directed towards the specific receptor to which entry is desired. This is in contrast to the initial screening strategy, where the virus can find any protein on the cell surface to bind and utilize as a receptor. The cell specificity is later determined on a panel of cells. Although each of these approaches has its benefits, it is hard to predict which will yield the best results. There are many aspects to retroviral entry which to date remain unknown and therefore cannot be manipulated by molecular biologists. Although targeting known prostate-specific proteins for entry decreases concerns about prostate specificity, yielding a higher degree of flexibility to the virus in choosing a receptor might prove more successful. The inverse screening protocol can also be adopted to alternative prostate specific proteins, such as prostate specific membrane antigen (PSM) (24).

Example 6

Insertion of cell binding peptides into the FeLV A-SU.

Another related strategy for targeting retroviral entry to specific cell types is to substitute the receptor-determining region of FeLV-A Env with peptides that bind to specific cell types. For example, oligopeptides which bind with high affinity to chemokine receptor-5 (CCR-5) have been identified (87, 88). CCR-5 is a coreceptor for HIV-1. Delivery of anti-HIV genes have been identified (87, 88). CCR-5 is a coreceptor for HIV-1. Delivery of anti-HIV genes such as ribozymes or intrabodies (89, 90) to cells expressing this receptor could inhibit HIV-1 replication in those cells. The size of these peptides (derived from the RANTES CCR-5 ligand) are suitable for substitution into the cell-binding domain of FeLV Env. The sequence of the VRA/Vr1 region of FeLV-A and a RANTES peptide sequence (underlined) flanked by random amino acids is shown below. Other peptides of similar length have also been identified (87, 88) and could be similarly incorporated into this region.

Since the CCR-5-binding peptides were originally identified unattached to any other protein, the conformation of the peptide might be different when placed onto the surface of the FeLV Env protein. In order to present the peptides in a favorable conformation, the peptides would be linked to the FeLV Env sequence via amino acids which could be randomized in order to create a library of Env proteins. The construct shown in FIG. 10 with 6 randomized positions would present the CCR-5 binding peptides in over $10^7$ different conformations. Altering the numbers of random amino acids on one side or the other of the peptide would also increase the number of ways of presenting the peptides. The primers encoding the CCR-5-binding peptide flanked by random sequences would be similar to those used for creating the random library described above. In this case, a fourth primer would be used to hybridize to the known CCR-5-binding peptide sequence, leaving only the randomized portions single-stranded. This strategy is similar to a previous strategy used to present antigenic HIV epitopes in different conformations on the surface of rhinovirus to use as immunogens (13).

Env proteins displaying RANTES peptides that successfully mediate gene transfer to CCR-5 expressing cells could be isolated using the system we have established for use with the random oligopeptide library discussed above. Viruses bearing these RANTES peptide/Env hybrids can be tested for their ability to mediate retroviral entry into cells expressing CCR-5 on their surface such as T-cells and macrophages. Once identified and characterized, these Env derivatives can be used to deliver anti-HIV genes to CCR-5 expressing cells. Whereas previous attempts to retarget retroviruses have relied on the investigation of a very small number of individually constructed Env-ligand derivatives, the ability to screen through a library of over a million different constructs at one time increases the chances of retrieving a retargeted Env protein.

References Referred to in Text by Numbers in Parentheses

2. Martiniello-Wilks, R., J. Garcia-Aragon, M. M. Daja, P. Russell, G. W. Both, P. L. Molloy, L. J. Lockett, and P. J. Russell, 1998. In vivo gene therapy for prostate cancer: preclinical evaluation of two different enzyme-directed pro-drug therapy systems delivered by identical adenovirus vectors. Hum. Gene Ther., 9: p. 1617–1626.

3. Hughes, B. W., A. H. Wells, Z. Bebok, V. K. Gadi, J. Garver, R. I., W. B. Parker, and E. J. Sorscher, 1995. Bystander killing of melanoma cells using the human tyrosinase promoter to express the *Escherichia coli* purine nucleoside phosphorylase gene. Cancer Res., 55: p. 3339–3345. G. M. Gersuk, et al., Biochem. Biophys. Res. Com. 232, 578–582 (1997).

4. Y. Soneoka, et al., Nuc. Acids Res. 23, 628–633 (1995).

5. Bae, Y., S. M. Kingsman, and A. J. Kingsman. 1997. Functional dissection of the Moloney murine leukemia virus envelope protein gp70. J. Virol. 71:2092–2099.

6. Battini, J.-L., O. Danos, and J. M. Heard. 1995. Receptor-binding domain of murine leukemia virus envelope glycoproteins. J. Virol. 69:713–719.

7. Battini, J.-L., J. M. Heard, and O. Danos. 1992. Receptor choice determinants in the envelope glycoproteins of amphotropic, xenotropic, and polytropic murine leukemia viruses. J. Virol. 66:1468–1474.

8. Battini L., P. Rodrigues, R. Muller, O. Danos, and J. M. Heard. 1996. Receptor-binding properties of a purified fragment of the 4070A amphotropic murine leukemia virus envelope glycoprotein. J. Virol. 70:4387–4393.

9. Battini, J. L., O. Danos, and J. M. Heard. 1998. Definition of a 14-amino-acid peptide essential for the interaction between the murine leukemia virus amphotropic envelope glycoprotein and its receptor. J. Virol. 72:428–435.

10. K. T. O'Neil, et al., Proteins 14, 509–515 (1992).

11. R. A. M. Fouchier, B. E. Meyer, J. H. M. Simon, U. Fischer, M. H. Malim, EMBO J. 16, 4531–4539 (1997).

12. F.-L. Cosset, Y. Takeuchi, J.-L. Battini, R. A. Weiss, M. K. L. Collins, Journal of Virology 69, 7430–7436 (1995).

13. A. D. Smith, et al., J. Virol. 72, 651–659 (1998).

14. J. F. Karr, J. A. Kantor, P. H. Hand, E. D. L., J. Schlom, Cancer Res. 55, 2455–2462 (1995).

15. C. Wei, et al., Cancer Immunol. Immunother. 42, 362–368 (1996).

16. C. Wei, et al., Proc. Natl. Acad. Sci. USA 94, 6369–6374 (1997).

17. O'Reilly, L. and M. J. Roth, 2000. Second-site changes affect viability of amphotropic/ecotropic chimeric-envelope MuLVs. J. Virol., 74: p. 899–913.

18. Pawelec, G., R. C. Rees, R. Kiessling, A. Madrigal, A. Dodi, C. Baxevanis, C. Gambacorti-Passerini, G. Masucci, and J. Zeuthen, 1999. Cells and cytokines in immunotherapy and gene therapy of cancer. Crit. Rev. Oncog., 10: p. 83–127.

19. Greenberg, N. M., F. J. DeMayo, P. C. Sheppard, R. Barrios, R. Lebovitz, M. Finegold, R. Angelopoulou, J. G. Dodd, M. L. Duckworth, J. M. Rosen, and R. J. Natusik, 1994. The rat probasin gene promoter directs hormonally and developmentally regulated expression of a heterologous gene specifically to the prostate in transgenic mice. Mol. Endocrinol., 8: p. 230–239.

20. Fassati, A., A. Bardoni, M. Sironi, D. J. Wells, N. Bresolin, G. Scarlato, M. Hatanaka, S. Yamaoka, and G. Dickson, 1998. Insertion of two independent enhancers in the long terminal repeat of a self-inactivating vector results in high-titer retroviral vectors with tissue-specific expression. Hum. Gene Ther., 9: p. 2459–2468.

21. Davey, R. A., C. A. Hamson, J. J. Healy, and J. M. Cunningham. 1997. In vitro binding of purified murine ecotropic retrovirus envelope surface protein to its receptor, MCAT-1. J. Virol. 71:8096–02.

22. Soneoka, Y., P. M. Cannon, E. E. Ramsdale, J. C. Griffiths, G. Romano, S. M. Kingsman, and A. J. Kingsman, 1995. A transient three-plasmid expression system for the production of high titer retroviral vectors. Nuc. Acids Res., 23: p. 628–633.

23. Hubert, R. S., I. Vivanco, E. Chen, S. Rastegar, K. Leong, S. C. Mitchell, Madraswala, Y. Zhou, J. Kuo, A. B. Raitano, A. Jakobovits, D. C. Saffran, and D. E. H. Afar, 1999. STEAP: A prostate-specific cell-surface antigen highly expressed in human prostate tumors. Proc. Natl. Acad. Sci. USA, 96: p. 14523–14528.

24. Israeli, R. S., C. T. Powell, J. G. Corr, W. R. Fair, and W. D. W. Heston, 1994. Expression of the prostate-specific membrane antigen. Cancer Res., 54: p. 1807–1811.

25. Somia, N. V., H. Miyoshi, M. J. Schmitt, and I. M. Verma, 2000. Retroviralvector targeting to human immunodeficiency virus type 1-infected cells by receptor pseudotyping. J. Virol., 74: p. 4420–4424.

26. Balliet, J. and P. Bates, 1998. Efficient infection mediated by viral receptors incorporated into retroviral particles. J. Virol., 72: p. 6671–676.

27. Fass, D., R. A. Davey, C. A. Hamson, P. S. Kim, J. M. Cunningham, and J. M. Berger. 1997. Structure of a murine leukemia virus receptor-binding glycoprotein at 2.0 Angstrom resolution. Science. 277:1662–1666.

28. Fass, D., S. C. Harrison, and P. S. Kim. 1996. Retrovirus envelope domain at 1.7 Å resolution. Nature Struct. Biol. 3:465–469.

30. Gray, K. D., and M. J. Roth. 1993. Mutational analysis of the envelope gene of Moloney murine leukemia virus. J. Virol. 67:3489–3496.

33. Han, J.-Y., P. M. Cannon, K.-M. Lai, Y. Zhao, M. V. Eiden, and W. F. Anderson. 1997. Identification of envelope protein residues required for the expanded host range of 10A1 murine leukemia virus. J. Virol. 71:8103–8108.

34. Han, J.-Y., Y. Zhao, W. F. Anderson, and P. M. Cannon. 1998. Role of variable regions A and B in receptor binding domain of amphotropic murine leukemia virus envelope protein. J. Virol. 72:9101–9108.

35. Han, L., T. Hofmann, Y. Chiang, and W. F. Anderson. 1995. Chimeric envelope glycoproteins constructed between amphotropic and xenotropic murine leukemia retroviruses. Som. Cell Mol. Genet. 21:205–214.

38. Heard, J. M., and O. Danos. 1991. An amino-terminal fragment of the Friend murine leukemia virus envelope glycoprotein binds the ecotropic receptor. J. Virol. 65:4026–4032.

49. Lee, S.-Y., T. M. Howard, and S. Rasheed. 1998. Genetic analysis of the rat leukemia virus: influence of viral sequences in transduction of the c-ras proto-oncogene and expression of its transforming activity. J. Virol. 72:9906–9917.

50. MacBeath, G., P. Kast, and D. Hilvert. 1998. Redesigning enzyme topology by directed evolution. Science. 279:1958–1961.

58. McClure, M. O., M. A. Sommerfelt, M. Marsh, and R. A. Weiss. 1990. The pH independence of mammalian retrovirus infection. J. Gen. Virol. 71:767–773.

65. Opstelten, D.-J. E., M. Wallin, and H. Garoff. 1998. Moloney murine leukemia virus envelope protein subunits, gp70 and Pr15E, form a stable disulfide-linked complex. J. Virol. 72:6537–6545.

67. Ott, D., and A. Rein. 1992. Basis for receptor specificity of nonecotropic murine leukemia virus surface glycoprotein gp70 SU. J. Virol. 66:4632–4638.

70. Peredo, C., L. O'Reilly, K. Gray, and M. J. Roth. 1996. Characterization of chimeras between the ecotropic Moloney murine leukemia virus and the amphotropic 4070A envelope proteins. J. Virol. 70:3142–3152.

71. Pinter, A., R. Kopelman, Z. Li, S. C. Kayman, and D. A. Sanders. 1997. Localization of the labile disulfide bond between SU and TM of the murine leukemia virus envelope protein complex to a highly conserved CWLC motif in SU that resembles the active-site sequence of thiol-disulfide exchange enzymes. J. Virol. 71:8073–8077.

77. Rigby, M. A., J. L. Rojko, M. A. Stewart, G. J. Kociba, C. M. Cheney, L. J. Rezanka, L. E. Mathes, J. R. Hartke, O. Jarrett, and J. C. Neil. 1992. Partial dissociation of subgroup C phenotype and in vivo behaviour in feline leukaemia viruses with chimeric envelope genes. J. Gen. Virol. 73:2839–2847.

86. Tailor, C. S., and D. Kabat. 1997. Variable regions A and B in the envelope glycoproteins of feline leukemia virus subgroup B and amphotropic murine leukemia virus interact with discrete receptor domains. J. Virol. 71:9383–9391.

87. Nishiyama, Y., Murakami, T., Kurita, K. and Yamamoto, N. (1997) Synthesis of some peptides corresponding to the active region of RANTES for chemotaxis and evaluation of their anti-human immunodeficiency virus-1 activity Chem. Pharm. Bull. 45: 2125–2127.

88. Wells, T. N. C., Guye-Coulin, F. and K. B. Bacon (1995) Peptides from the amino-terminus of RANTES cause chemotaxis of human T-lymphocytes. Biochem. Biophys. Res. Comm. 211: 100–105.

89. Gervaix, A., X. Li, G. Kraus and F. Wong-Staal (1997) Multigene antiviral vectors inhibit diverse human immunodeficiency virus type 1 clades. J. Virol. 71: 3048–3053.

90. Marasco, W. A., J. LaVecchio, and A. Winkler (1999) Human anti-HIV-1 tat sFv intrabodies for gene therapy of advanced HIV-1-infection and AIDS. J. Immunol. Methods 10: 223–238.

What is claimed is:

1. A method of identifying a retrovirus expressing a FeLV-A or FeLV-C Env variant on its surface capable of transferring its nucleic acid to a host cell, said method comprising the steps of:

(1) infecting a population of host cells with a random display library of retroviruses comprising a plurality of retroviruses, wherein each retrovirus differs in relation to other retroviruses of the plurality as to an amino acid sequence of an exterior protein, wherein said exterior protein is an Env variant consisting of a variable region A (VRA) with a random amino acid sequence, and wherein said infecting of said host cell population leads to transfer of retroviral nucleic acid to said host cell population;

(2) assaying for retroviral reverse transcriptase in a cell supernatant of said host cell population infected with said random display library of retroviruses, wherein detecting retroviral reverse transcriptase indicates a presence of a retrovirus expressing a FeLV-A or FeLV-C Env variant on its surface, wherein expressing said FeLV-A or FeLV-C Env variant on its surface renders said retrovirus capable of infecting a host cell in said host cell population, and (3) isolating host cell colonies from said host cell population and assaying cell supernatants of isolated host cell colonies for retroviral reverse transcriptase, wherein detection of retroviral reverse transcriptase in a cell supernatant of an isolated host cell colony indicates that said isolated host cell colony is infected with a retrovirus expressing a FeLV-A or FeLV-C Env variant on its surface, and thereby identifies a retrovirus expressing a FeLV-A or FeLV-C Env variant on its surface capable of transferring its nucleic acid to a host cell.

2. A method of identifying a retrovirus expressing a FeLV-A or FeLV-C Env variant on its surface capable of transferring its nucleic acid to a host cell, said method comprising the steps of:

(1) infecting a population of host cells with a random display library of retroviruses comprising a plurality of retroviruses, wherein each retrovirus of the plurality comprises a nucleic acid sequence encoding a FeLV-A or FeLV-C Env variant and a cell-selection marker, and each retrovirus differs in relation to other retroviruses of the plurality as to an amino acid sequence of a FeLV-A or FeLV-C Env protein, said FeLV-A or FeLV-C Env protein consisting of a variable region A (VRA) with a random amino acid sequence;

(2) selecting for retrovirus-infected cells expressing the cell-selection marker, wherein expression of said cell-selection marker distinguishes retrovirus-infected cells from uninfected cells in said host cell population; and (3) isolating said retrovirus-infected cells to identify a retrovirus expressing a FeLV-A or FeLV-C Env variant on its surface capable of transferring its nucleic acid to a host cell.

3. The method of claim 1 or 2 wherein the plurality of retroviruses is at least $1 \times 10^5$.

* * * * *

SEQUENCE LISTING

<160> NUMBER OF SEQ ID NOS: 27

<210> SEQ ID NO 1
<211> LENGTH: 65
<212> TYPE: PRT
<213> ORGANISM: moloney murine leukemia virus

<400> SEQUENCE: 1

His Gly Pro Ser Tyr Trp Gly Leu Glu Tyr Gln Ser Pro Phe Ser Ser
1               5                   10                  15

Pro Pro Gly Pro Pro Cys Cys Ser Gly Gly Ser Ser Pro Gly Cys Ser
            20                  25                  30

Arg Asp Cys Glu Glu Pro Leu Thr Ser Leu Thr Pro Arg Cys Asn Thr
        35                  40                  45

Ala Trp Asn Arg Leu Lys Leu Asp Gln Thr Thr His Lys Ser Asn Glu
    50                  55                  60

Gly
65

<210> SEQ ID NO 2
<211> LENGTH: 11
<212> TYPE: PRT
<213> ORGANISM: moloney murine leukemia virus

<400> SEQUENCE: 2

Ser Asp Gln Ala Val Gln Val Cys Lys Asp Asn
1               5                   10

<210> SEQ ID NO 3
<211> LENGTH: 9
<212> TYPE: PRT
<213> ORGANISM: moloney murine leukemia virus

<400> SEQUENCE: 3

Pro His Arg Pro Arg Glu Ser Lys Ser
1               5

<210> SEQ ID NO 4
<211> LENGTH: 29
<212> TYPE: PRT
<213> ORGANISM: amphotropic murine leukemia virus

<400> SEQUENCE: 4

Glu Glu Trp Asp Pro Ser Asp Gln Glu Pro Tyr Val Gly Tyr Gly Cys
1               5                   10                  15

Lys Tyr Pro Ala Gly Arg Gln Arg Thr Arg Thr Phe Asp
            20                  25

<210> SEQ ID NO 5
<211> LENGTH: 30
<212> TYPE: PRT
<213> ORGANISM: amphotropic murine leukemia virus

<400> SEQUENCE: 5

Pro Trp Asp Thr Gly Cys Ser Lys Val Ala Cys Gly Pro Cys Tyr Asp
1               5                   10                  15

Leu Ser Lys Val Ser Asn Ser Phe Gln Gly Ala Thr Arg Gly
            20                  25                  30

<210> SEQ ID NO 6

```
<211> LENGTH: 6
<212> TYPE: PRT
<213> ORGANISM: amphotropic murine leukemia virus

<400> SEQUENCE: 6

His Thr Val Lys Ser Gly
1               5

<210> SEQ ID NO 7
<211> LENGTH: 39
<212> TYPE: PRT
<213> ORGANISM: Feline leukemia virus

<400> SEQUENCE: 7

Asp Thr Trp Glu Pro Ile Val Leu Asn Pro Thr Asn Val Lys His Gly
1               5                   10                  15

Ala Arg Tyr Ser Ser Lys Tyr Gly Cys Lys Thr Thr Asp Arg Lys
            20                  25                  30

Lys Gln Gln Gln Thr Tyr Pro
        35

<210> SEQ ID NO 8
<211> LENGTH: 6
<212> TYPE: PRT
<213> ORGANISM: Feline Leukemia Virus

<400> SEQUENCE: 8

Gln Asp Asn Ser Cys Glu
1               5

<210> SEQ ID NO 9
<211> LENGTH: 11
<212> TYPE: PRT
<213> ORGANISM: Feline Leukemia Virus

<400> SEQUENCE: 9

His Ala Pro Ser Leu Gly Pro Lys Gly Thr His
1               5                   10

<210> SEQ ID NO 10
<211> LENGTH: 21
<212> TYPE: PRT
<213> ORGANISM: Rat Leukemia Virus

<400> SEQUENCE: 10

Asp Ser Trp Glu His Thr Glu Arg Thr Pro His Asn Ser Tyr Pro Pro
1               5                   10                  15

Cys Arg His Ser Asp
            20

<210> SEQ ID NO 11
<211> LENGTH: 6
<212> TYPE: PRT
<213> ORGANISM: Rat Leukemia Virus

<400> SEQUENCE: 11

Gly Lys Arg Thr Arg Glu
1               5

<210> SEQ ID NO 12
<211> LENGTH: 24
<212> TYPE: PRT
<213> ORGANISM: Feline Leukemia Virus
```

-continued

```
<400> SEQUENCE: 12

Trp Glu Pro Ile Val Leu Asp Pro Thr Asn Val Lys His Gly Ala Arg
1               5                   10                  15

Tyr Pro Ser Ser Lys Tyr Gly Cys
            20

<210> SEQ ID NO 13
<211> LENGTH: 21
<212> TYPE: PRT
<213> ORGANISM: Feline Leukemia Virus

<400> SEQUENCE: 13

Trp Glu Pro Met Ala Pro Asp Pro Arg Ser Trp Ala Arg Tyr Ser Ser
1               5                   10                  15

Ser Ile His Gly Cys
            20

<210> SEQ ID NO 14
<211> LENGTH: 21
<212> TYPE: PRT
<213> ORGANISM: Artificial Sequence
<220> FEATURE:
<223> OTHER INFORMATION: Consensus Sequence
<221> NAME/KEY: Variant
<222> LOCATION: (10) through (14)
<223> OTHER INFORMATION: Xaa is any amino acid.
<221> NAME/KEY: Variant
<222> LOCATION: (4) through (8)
<223> OTHER INFORMATION: Xaa is any amino acid.

<400> SEQUENCE: 14

Trp Glu Pro Xaa Xaa Xaa Xaa Xaa Arg Xaa Xaa Xaa Xaa Xaa Ser Ser
1               5                   10                  15

Ser Lys Tyr Gly Cys
            20

<210> SEQ ID NO 15
<211> LENGTH: 14
<212> TYPE: PRT
<213> ORGANISM: Amphotropic Murine Leukemia Virus

<400> SEQUENCE: 15

Glu Glu Trp Asp Pro Ser Asp Gln Glu Pro Tyr Val Gly Tyr
1               5                   10

<210> SEQ ID NO 16
<211> LENGTH: 13
<212> TYPE: PRT
<213> ORGANISM: Amphotropic Murine Leukemia Virus

<400> SEQUENCE: 16

Pro Trp Asp Thr Gly Cys Ser Lys Val Ala Cys Gly Pro
1               5                   10

<210> SEQ ID NO 17
<211> LENGTH: 29
<212> TYPE: PRT
<213> ORGANISM: Amphotropic Murine Leukemia Virus

<400> SEQUENCE: 17

Val Gly Asp Thr Trp Glu Pro Ile Val Leu Asn Pro Thr Asn Val Lys
1               5                   10                  15

His Gly Ala Arg Tyr Ser Ser Ser Lys Tyr Gly Cys Lys
            20                  25
```

<210> SEQ ID NO 18
<211> LENGTH: 26
<212> TYPE: PRT
<213> ORGANISM: Feline Leukemia Virus

<400> SEQUENCE: 18

Val Gly Thr Asp Trp Glu Pro Met Ala Pro Asp Pro Arg Ser Trp Ala
1               5                   10                  15

Arg Tyr Ser Ser Ser Thr His Gly Cys Lys
            20                  25

<210> SEQ ID NO 19
<211> LENGTH: 19
<212> TYPE: PRT
<213> ORGANISM: Feline Leukemia Virus

<400> SEQUENCE: 19

Val Gly Glu Glu Trp Asp Pro Ser Asp Gln Glu Pro Tyr Val Gly Tyr
1               5                   10                  15

Gly Cys Lys

<210> SEQ ID NO 20
<211> LENGTH: 72
<212> TYPE: DNA
<213> ORGANISM: Artificial Sequence
<220> FEATURE:
<223> OTHER INFORMATION: example of variable insertion site
<223> OTHER INFORMATION: n is any nucleotide.
<221> NAME/KEY: Variant
<222> LOCATION: (22) through (36)
<223> OTHER INFORMATION: n is any nucleotide.
<221> NAME/KEY: Variant
<222> LOCATION: (40) through (54)
<223> OTHER INFORMATION: n is any nucleotide.

<400> SEQUENCE: 20
gtgggagaca cctgggaacc tnnnnnnnnn nnnnnnagan nnnnnnnnnn nnnntcctcc         60
tcaaaatatg ga                                                            72

<210> SEQ ID NO 21
<211> LENGTH: 17
<212> TYPE: DNA
<213> ORGANISM: Feline Leukemia Virus

<400> SEQUENCE: 21
ctctgtggac ccttgga                                                       17

<210> SEQ ID NO 22
<211> LENGTH: 22
<212> TYPE: DNA
<213> ORGANISM: Feline Leukemia Virus

<400> SEQUENCE: 22
aggaggagtt ttatacctac at                                                 22

<210> SEQ ID NO 23
<211> LENGTH: 25
<212> TYPE: PRT
<213> ORGANISM: Homo sapiens
<220> FEATURE:
<221> NAME/KEY: Variant
<222> LOCATION: (4) through (6)
<223> OTHER INFORMATION: Xaa is any amino acid.
<221> NAME/KEY: Variant -continued

```
<222> LOCATION: (17 through (19)
<223> OTHER INFORMATION: Xaa is any amino acid.

<400> SEQUENCE: 23

Trp Glu Pro Xaa Xaa Xaa Ser Pro Tyr Ser Ser Asp Thr Thr Pro Ala
1               5                   10                  15

Xaa Xaa Xaa Ser Ser Lys Tyr Gly Cys
            20                  25

<210> SEQ ID NO 24
<211> LENGTH: 25
<212> TYPE: PRT
<213> ORGANISM: Amphotropic Murine Leukemia Virus

<400> SEQUENCE: 24

Glu Glu Trp Asp Pro Ser Asp Gln Glu Pro Tyr Val Gly Tyr Gly Cys
1               5                   10                  15

Lys Tyr Pro Ala Gly Arg Gln Arg Thr
            20                  25

<210> SEQ ID NO 25
<211> LENGTH: 29
<212> TYPE: PRT
<213> ORGANISM: Amphotropic Murine Leukemia Virus

<400> SEQUENCE: 25

Pro Trp Asp Thr Gly Cys Ser Lys Val Ala Cys Gly Pro Cys Tyr Asp
1               5                   10                  15

Leu Ser Lys Val Ser Asn Ser Phe Gln Gly Ala Thr Arg
            20                  25

<210> SEQ ID NO 26
<211> LENGTH: 10
<212> TYPE: PRT
<213> ORGANISM: Homo sapiens

<400> SEQUENCE: 26

Ser Pro Tyr Ser Ser Asp Thr Thr Pro Ala
1               5                   10

<210> SEQ ID NO 27
<211> LENGTH: 23
<212> TYPE: PRT
<213> ORGANISM: Moloney Mink Cell Focus-Inducing Virus

<400> SEQUENCE: 27

Asp Leu Ile Gly Asp Asp Trp Asp Glu Thr Gly Leu Gly Cys Arg Thr
1               5                   10                  15

Pro Gly Gly Arg Lys Arg Ala
            20
```